United States Patent [19]

Taylor et al.

[11] Patent Number: 6,013,245

[45] Date of Patent: Jan. 11, 2000

[54] AEROSOL FORMULATION CONTAINING BECLOMETHASONE DIPROPIONATE AND 1,1,1,2,3,3,3-HEPTAFLUORO-N-PROPANE AS PROPELLANT

[75] Inventors: Anthony James Taylor; Philip John Neale, both of Ware, United Kingdom

[73] Assignee: Glaxo Group Limited, Greenford, United Kingdom

[21] Appl. No.: 09/139,115

[22] Filed: Aug. 24, 1998

Related U.S. Application Data

[63] Continuation of application No. 08/877,796, Jun. 18, 1997, Pat. No. 5,833,950, which is a continuation of application No. 08/373,267, Jan. 26, 1995, abandoned.

[51] Int. Cl.[7] .................................................. A61K 9/12
[52] U.S. Cl. ................................. 424/45; 424/46
[58] Field of Search ........................... 424/45, 46

[56] References Cited

U.S. PATENT DOCUMENTS

| | | | |
|---|---|---|---|
| 4,044,126 | 8/1977 | Cook et al. | 424/243 |
| 4,810,488 | 3/1989 | Jinks | 424/45 |
| 5,118,494 | 6/1992 | Schultz et al. | 424/45 |
| 5,589,156 | 12/1996 | Henry | 424/45 |
| 5,605,674 | 2/1997 | Purewal et al. | 424/45 |
| 5,653,961 | 8/1997 | McNally et al. | 424/45 |
| 5,653,962 | 8/1997 | Akehurst et al. | 424/45 |
| 5,658,549 | 8/1997 | Akehurst et al. | 424/45 |
| 5,674,471 | 10/1997 | Akehurst et al. | 424/45 |
| 5,674,472 | 10/1997 | Akehurst et al. | 424/45 |
| 5,676,929 | 10/1997 | Akehurst et al. | 424/45 |
| 5,683,676 | 11/1997 | Akehurst et al. | 424/45 |
| 5,688,782 | 11/1997 | Neale et al. | 514/180 |

FOREIGN PATENT DOCUMENTS

| | | | |
|---|---|---|---|
| 0372777 | 6/1990 | European Pat. Off. | |
| 0518600 | 12/1992 | European Pat. Off. | 424/45 |
| 11495 | 8/1991 | WIPO | |
| 93/11743 | 6/1993 | WIPO | |

*Primary Examiner*—Raj Bawa
*Attorney, Agent, or Firm*—Bacon & Thomas

[57] ABSTRACT

The present invention relates to a pharmaceutical aerosol formulation which comprises particulate anhydrous beclomethasone dipropionate together with 1,1,1,2,3,3,3-heptafluoro-n-propane as propellant, which formulation is free of surfactant. The formulation may also contain salbutamol and includes a canister suitable for delivery and a method of treating respiratory disorders administering the formulation by inhalation.

13 Claims, No Drawings

AEROSOL FORMULATION CONTAINING BECLOMETHASONE DIPROPIONATE AND 1,1,1,2,3,3,3-HEPTAFLUORO-N-PROPANE AS PROPELLANT

This application is a continuation of 08/877,796 filed Jun. 18, 1997, now U.S. Pat. No. 5,833,950, which is a continuation of U.S. application Ser. No. 08/373,267 filed Jan. 26, 1995 now abandoned.

BACKGROUND OF THE INVENTION

This invention relates to novel aerosol formulations for administering drugs, in particular for administration of a beclomethasone ester by inhalation.

Beclomethasone dipropionate is 9α-chloro-16β-methyl-1,4-pregnadiene-11β, 17α,21-triol-3,20-dione 17α,21-dipropionate and may be represented by the formula (I)

The corticosteroid of formula (I) is known to exhibit topical antiinflammatory activity and is useful in the treatment of asthmatic conditions, particularly in the form of aerosol formulations. The use of such formulations is described in GB-1429184 where it is noted that micronised anhydrous beclomethasone dipropionate tends to display crystal growth, due to solvate formation, when incorporated into aerosol formulations containing chlorofluorocarbon propellants. Crystals having a particle size of more than 20 microns were shown to be too large to penetrate the bronchial system and prone to cause clogging of the metering valve making them unsuitable for administration by inhalation.

A number of potential solutions to this problem have been proposed. These include the use of micronised solvates of beclomethasone dipropionate, for example chlorofluorocarbon solvates (GB-1429184), ethyl acetate solvate (DE-3018550OS), $C_{5-8}$ alkane solvates (EP-0039369), diisopropyl ether solvate (EP-0172672) and $C_{1-5}$ alcohol solvates (WO86/03750). GB-2076422A discloses a process for the preparation of chlorofluorocarbon aerosols which incorporates a low temperature (5 to −40° C.) step which is also claimed to inhibit crystal growth.

An alternative solution to the problem of crystal growth in aerosol formulations containing beclomethasone dipropionate has recently been disclosed in WO92/06675. This document describes the preparation of aerosol formulations containing solutions of beclomethasone dipropionate in ethanol, together with hydrofluorocarbon 134a (1,1,1,2-tetrafluoroethane) or hydrofluorocarbon 227 (1,1,1,2,3,3,3-heptafluoropropane) as propellant. Since a solution of beclomethasone dipropionate in ethanol is employed in the aerosols rather than a suspension of particulate beclomethasone diproprionate, elaborate process steps or the preparation of a solvate of the active ingredient prior to incorporation into the aerosol formulation is not required.

Nevertheless, whilst ethanol is pharmaceutically acceptable and generally recognised as safe, it is associated with a number of disadvantages which may restrict is use. In particular, administration of ethanol-containing products to teetotal or alcohol-dependent individuals or to children is undesirable.

A number of other patent applications describe the preparation of aerosol formulations containing drug and a fluorocarbon propellant, together with the addition of one or more adjuvants such as surfactants. Thus, for example WO91/14422 describes the preparation of aerosol formulations containing beclomethasone dipropionate in the form of its 1,1,1,2-tetrafluoroethane clathrate together with 1,1,1,2-tetrafluoroethane and various surface-active dispersing agents.

We have now found that certain novel aerosol formulations containing particulate beclomethasone diproprionate are surprisingly stable without recourse to the use of any adjuvant or cosolvent in the composition.

BRIEF SUMMARY OF THE INVENTION

The present invention therefore provides a pharmaceutical aerosol formulation which comprises particulate beclomethasone dipropionate or a pharmaceutically acceptable solvate thereof together with a fluorocarbon or hydrogen-containing chlorofluorocarbon propellant, which formulation is substantially free of surfactant. By "substantially free of surfactant" is meant formulations which contain no significant amounts of surfactant, for example less than 0.0001% by weight of the beclomethasone dipropionate.

DETAILED DESCRIPTION OF INVENTION

The particle size of the particulate beclomethasone dipropionate may be reduced by conventional methods, for example by micronisation, fluid energy milling or ball milling and should be such as to permit inhalation of substantially all of the drug into the lungs upon administration of the aerosol formulation. Preferably the particle size of the beclomethasone dipropionate will be less than 20 microns, most preferably less than 10 microns, in particular in the range of 1 to 5 microns.

Suitable pharmaceutically acceptable solvates of beclomethasone dipropionate include solvates with chlorofluorocarbons, ethyl acetate, alkanes, ethers, alcohols and water. However, beclomethasone dipropionate is preferably used in the form of a solvate with 1,1,1,2-tetrafluoroethane ($CF_3CH_2F$).

The term "beclomethasone dipropionate-1,1,1,2-tetrafluoroethane solvate" as used herein refers to any crystalline material in which beclomethasone dipropionate and 1,1,1,2-tetrafluoroethane are associated. The ratio of the steroid to the solvating species need not be stoichiometric and no particular mechanism of association is implied. The solvate may contain, for example, from about 20 to about 30% by weight of 1,1,1,2-tetrafluoroethane, the precise amount depending on the particular method of preparation used.

Preferably the solvate is prepared by intimate admixture of beclomethasone dipropionate with 1,1,1,2-tetrafluoroethane to form a crystalline solvate therewith. The process is desirably carried out in the absence of other potential solvating species such as water, alcohol, chlorofluorocarbons, ethyl acetate, alkane and diisopropyl ether. Thus, for example, micronised beclomethasone dipropionate may be contacted with dry, preferably liquified, 1,1,1,2-tetrafluoroethane. The crystalline solvate formed can be obtained by conventional means such as filtration and drying.

We have found that the beclomethasone dipropionate-1,1,1,2-tetrafluoroethane solvate is surprisingly stable at ambient temperatures and pressures. In particular, beclomethasone dipropionate-1,1,1,2-tetrafluoroethane solvate has been found to be stable at temperatures up to about 65° C. The particle size of the crystalline solvate may be reduced by conventional methods, for example by micronisation, fluid energy milling or ball milling and should be such as to permit inhalation of substantially all of the medicament into the lungs. Preferably the particle size of the solvate is reduced in an atmosphere or partial atmosphere of 1,1,1,2-tetrafluoroethane. The solvate in micronised form may be incorporated into aerosol formulations and unexpectedly does not exhibit any significant crystal growth or agglomeration. Furthermore, the solvate appears to be more easily wetted than the anhydrous or other known solvates of beclomethasone dipropionate in 1,1,1,2-tetrafluoroethane enabling the preparation of aerosols with improved dispersion characteristics.

Accordingly, one particular aspect of the invention provides a pharmaceutical aerosol formulation which comprises particulate beclomethasone dipropionate-1,1,1,2-tetrafluoroethane solvate together with a fluorocarbon or hydrogen-containing chlorofluorocarbon propellant, which formulation is substantially free of surfactant.

The propellants for use in the invention may be any fluorocarbon or hydrogen-containing chlorofluorocarbon or mixtures thereof having a sufficient vapour pressure to render them effective as propellants. Preferably the propellant will be a non-solvent for the medicament. Suitable propellants include for example $C_{1-4}$ hydrogen-containing chlorofluorocarbons such as $CH_2ClF$, $CClF_2CHClF$, $CF_3CHClF$, $CHF_2CClF_2$, $CHClFCHF_2$, $CF_3CH_2Cl$ and $CClF_2CH_3$, $C_{1-4}$ hydrogen-containing fluorocarbons such as $CHF_2CHF_2$, $CF_3CH_2F$, $CHF_2CH_3$ and $CF_3CHFCF_3$ and $C_{1-4}$ perfluorocarbons such as $CF_3CF_3$ and $CF_3CF_2CF_3$.

Where mixtures of the fluorocarbons or hydrogen-containing chlorofluorocarbons are employed they may be mixtures of the above identified compounds or mixtures, preferably binary mixtures, with other fluorocarbons or hydrogen-containing chlorofluorocarbons for example $CHClF_2$, $CH_2F_2$ and $CF_3CH_3$.

Preferably a single fluorocarbon or hydrogen-containing chlorofluorocarbon is employed as the propellant. Particularly preferred as propellants are hydrogen-containing fluorocarbons, especially 1,1,1,2-tetrafluoroethane ($CF_3CH_2F$) and 1,1,1,2,3,3,3-heptafluoro-n-propane ($CF_3CHFCF_3$).

It is desirable that the formulations of the invention contain no components which may provoke the degradation of stratospheric ozone. In particular it is desirable that the formulations are substantially free of chlorofluorocarbons especially non hydrogen-containing chlorofluorocarbons such as $CCl_3F$, $CCl_2F_2$ and $CF_3CCl_3$. As used herein "substantially free" means less than 1% w/w based upon the fluorocarbon or hydrogen-containing chlorofluorocarbon propellant, in particular less than 0.5%, for example 0.1% or less.

The propellant may optionally contain an adjuvant having a higher polarity and/or a higher boiling point than the propellant. Polar adjuvants which may be used include (e.g. $C_{2-6}$) aliphatic alcohols and polyols such as ethanol, isopropanol and propylene glycol, preferably ethanol. In general only small quantities of polar adjuvants (e.g. 0.05–3.0% w/w) are required to improve the stability of the dispersion—the use of quantities in excess of 5% w/w may tend to dissolve the medicament. Formulations in accordance with the invention preferably contain less than 1% w/w, e.g. about 0.1% w/w or less, of polar adjuvants. Suitable volatile adjuvants include saturated hydrocarbons such as propane, n-butane, isobutane, pentane and isopentane and alkyl ethers such as dimethyl ether. In general, up to 50% w/w of the propellant may comprise a volatile adjuvant, for example 1 to 30% w/w of a volatile saturated $C_{1-6}$ hydrocarbon.

However, it is preferable that the formulations of the invention are substantially free of other potential solvating species such as chlorofluorocarbons, ethyl acetate, alkanes, ethers, alcohols and water. In particular, the formulations are substantially free of water, for example containing less than 250 ppm, preferably less than 200 ppm, more preferably less than 100 ppm, for example less than 50 ppm water.

A particularly preferred embodiment of the invention provides a pharmaceutical aerosol formulation which consists essentially of beclomethasone dipropionate-1,1,1,2-tetrafluoroethane solvate and one or more fluorocarbon or hydrogen-containing chlorofluorocarbon propellants, particularly 1,1,1,2-tetrafluoroethane.

Alternatively, the beclomethasone dipropionate may be employed in anhydrous form in the compositions according to the invention. Thus, a further aspect of the invention provides a pharmaceutical aerosol formulation which comprises particulate anhydrous beclomethasone dipropionate together with a fluorocarbon or hydrogen-containing chlorofluorocarbon propellant, which formulation is substantially free of surfactant.

A particularly preferred embodiment of the invention provides a pharmaceutical aerosol formulation which consists essentially of anhydrous beclomethasone dipropionate and 1,1,1,2,3,3,3-heptafluoro-n-propane as propellant.

The final aerosol formulation desirably contains 0.005–10% w/w, preferably 0.005–5.0% w/w, especially 0.01–1.0% w/w, for example 0.01–0.5% w/w of beclomethasone dipropionate relative to the total weight of the formulation.

It will be appreciated by those skilled in the art that the aerosol formulations according to the invention may, if desired, contain one or more additional active ingredients. Aerosol compositions containing two active ingredients (in a conventional propellant system) are known, for example, for the treatment of respiratory disorders such as asthma. Accordingly the present invention further provides aerosol formulations in accordance with the invention which contain one or more additional particulate medicaments. Additional medicaments may be selected from any other suitable drug useful in inhalation therapy and which may be presented in a form which is substantially completely insoluble in the selected propellant. Appropriate medicaments may thus be selected from, for example, analgesics, e.g. codeine, dihydromorphine, ergotamine, fentanyl or morphine; anginal preparations, e.g. diltiazem; antiallergics, e.g. cromoglycate, ketotifen or nedocromil; antiinfectives e.g. cephalosporins, penicillins, streptomycin, sulphonamides, tetracyclines and pentamidine; antihistamines, e.g. methapyrilene; anti-inflammatories, e.g. fluticasone, flunisolide, budesonide, tipredane or triamcinolone acetonide; antitussives, e.g. noscapine; bronchodilators, e.g. salmeterol, salbutamol, ephedrine, adrenaline, fenoterol, formoterol, isoprenaline, metaproterenol, phenylephrine, phenylpropanolamine, pirbuterol, reproterol, rimiterol, terbutaline, isoetharine, tulobuterol, orciprenaline, or (−)-4-amino-3,5-dichloro-α-[[[6-[2-(2-pyridinyl)ethoxy]hexyl]-amino]methyl]benzenemethanol; diuretics, e.g. amiloride; anticholinergics e.g. ipratropium, atropine or oxitropium; hormones, e.g. cortisone, hydrocortisone or prednisolone; xanthines e.g. aminophylline, choline theophyllinate, lysine theophyllinate or theophylline; and therapeutic proteins and peptides, e.g. insulin or glucagon. It will be clear to a person skilled in the art that, where appropriate, the medicaments may be used in the form of salts (e.g. as alkali metal or amine salts or as acid addition salts) or as esters (e.g. lower alkyl esters) or as solvates (e.g. hydrates) to optimise the activity and/or stability of the medicament and/or to minimise the solubility of the medicament in the propellant.

Particularly preferred aerosol formulations contain salbutamol (e.g. as the free base or the sulphate salt) or salmeterol (e.g. as the xinafoate salt) in combination with the beclomethasone diproprionate. Combinations of salmeterol xinafoate and beclomethasone dipropionate are preferred.

The formulations of the invention may be prepared by dispersal of the medicament in the selected propellant in an appropriate container, e.g. with the aid of sonication.

Minimising and preferably avoiding the use of formulation excipients e.g. surfactants, cosolvents etc in the aerosol formulations according to the invention is advantageous since the formulations may be substantially taste and odour free, less irritant and less toxic than conventional formulations.

The chemical and physical stability and the pharmaceutical acceptability of the aerosol formulations according to the invention may be determined by techniques well known to those skilled in the art. Thus, for example, the chemical stability of the components may be determined by HPLC assay, for example, after prolonged storage of the product. Physical stability data may be gained from other conventional analytical techniques such as, for example, by leak testing, by valve delivery assay (average shot weights per actuation), by dose reproducibility assay (active ingredient per actuation) and spray distribution analysis.

The formulations according to the invention may be filled into canisters suitable for delivering pharmaceutical aerosol formulations. Canisters generally comprise a container capable of withstanding the vapour pressure of the propellant used such as a plastic or plastic-coated glass bottle or preferably a metal can, for example an aluminium can which may optionally be anodised, lacquer-coated and/or plastic-coated, which container is closed with a metering valve. The metering valves are designed to deliver a metered amount of the formulation per actuation and incorporate a gasket to prevent leakage of propellant through the valve. The gasket may comprise any suitable elastomeric material such as for example low density polyethylene, chlorobutyl, black and white butadiene-acrylonitrile rubbers, butyl rubber and neoprene. Suitable valves are commercially available from manufacturers well known in the aerosol industry, for example, from Valois, France (e.g. DF10, DF30, DF60), Bespak plc, UK (e.g. BK300, BK356, BK357) and 3M-Neotechnic Ltd, UK (e.g. Spraymiser™).

Conventional bulk manufacturing methods and machinery well known to those skilled in the art of pharmaceutical aerosol manufacture may be employed for the preparation of large scale batches for the commercial production of filled canisters. Thus, for example, in one bulk manufacturing method a metering valve is crimped onto an aluminium can to form an empty canister. The particulate medicament is added to a charge vessel and liquified propellant is pressure filled through the charge vessel into a manufacturing vessel. The drug suspension is mixed before recirculation to a filling machine and an aliquot of the drug suspension is then filled through the metering valve into the canister. Typically, in batches prepared for pharmaceutical use, each filled canister is check-weighed, coded with a batch number and packed into a tray for storage before release testing.

Each filled canister is conveniently fitted into a suitable channelling device prior to use to form a metered dose inhaler for administration of the medicament into the lungs or nasal cavity of a patient. Suitable channelling devices comprise for example a valve actuator and a cylindrical or cone-like passage through which medicament may be delivered from the filled canister via the metering valve to the nose or mouth of a patient e.g. a mouthpiece actuator. Metered dose inhalers are designed to deliver a fixed unit dosage of medicament per actuation or "puff", for example in the range of 10 to 5000 microgram medicament per puff.

Administration of medicament may be indicated for the treatment of mild, moderate or severe acute or chronic symptoms or for prophylactic treatment. It will be appreciated that the precise dose administered will depend on the age and condition of the patient, the particular particulate medicament used and the frequency of administration and will ultimately be at the discretion of the attendant physician. When combinations of medicaments are employed the dose of each component of the combination will in general be that employed for each component when used alone. Typically, administration may be one or more times, for example from 1 to 8 times per day, giving for example 1,2,3 or 4 puffs each time.

Suitable daily doses, may be, for example in the range 100 to 2000 microgram of beclomethasone dipropionate, depending on the severity of the disease.

Thus, for example, each valve actuation may deliver 50, 100, 200 or 250 microgram beclomethasone dipropionate. Typically each filled canister for use in a metered dose inhaler contains 100, 160 or 240 metered doses or puffs of medicament.

The filled canisters and metered dose inhalers described herein comprise further aspects of the present invention.

A still further aspect of the present invention comprises a method of treating respiratory disorders such as, for example, asthma, which comprises administration by inhalation of an effective amount of a formulation as herein described.

The following non-limitative Examples serve to illustrate the invention.

EXAMPLE 1

Beclomethasone dipropionate-1,1,1,2-tetrafluoroethane solvate

Micronised anhydrous beclomethasone dipropionate (25.2 mg) was weighed into a clean dry plastic-coated glass bottle and dry (<50 ppm $H_2O$) 1,1,1,2-tetrafluoroethane (to 18.2 g) was added from a vacuum flask. The bottle was quickly sealed with a blank aluminium ferrule. The bottle was allowed to stand at ambient temperature. After several days crystals of the solvate formed were isolated by filtration.

The solvate thus obtained was analysed by various techniques.

Microscopic examination of the solvate showed the crystals to be columnar and prismatic and up to 500 to 1000 microns in length.

The solid state infra-red spectrum of the solvate was analysed. The most obvious differences between this spectrum and the solid state infra-red spectrum of anhydrous beclomethasone dipropionate were as follows:

(a) The broad OH band at 3300 cm$^{-1}$ is raised to near 3500 cm$^{-1}$ and is sharpened;

(b) The carbonyl band at 1750 cm$^{-1}$ is split into three distinct peaks indicating the solvated form; and (c) The 1,4-diene peaks are more widely separated with the 1610 cm$^{-1}$ peak moved up to about 1630 cm$^{-1}$.

Other differences were also apparent throughout the whole region examined with most peaks changed in position and intensity after solvation.

Thermogravimetric analysis and differential scanning calorimetry of the solvate at atmospheric pressure was carried out using a Netzsch Simultaneous Thermal Analyser STA409. Loss of 1,1,1,2-tetrafluoroethane started to occur at 65° C. Heat absorption continued to about 90° C. when an exothermic change resulted from 90° to 110° C. which corresponded with completion of the loss of 1,1,1,2-tetrafluoroethane at 120° C. This profile differs significantly from that of the known beclomethasone dipropionate-trichlorofluoromethane solvate in which trichlorofluoromethane loss starts to occur at 30° C.

The thermogravimetric analysis showed a total weight loss of 23.1% on heating the beclomethasone dipropionate-1,1,1,2- tetrafluoroethane solvate indicating a ratio of 3 molecules of 1,1,1,2-tetrafluoroethane to 2 molecules of beclomethasone dipropionate.

EXAMPLE 2

Beclomethasone dipropionate-1,1,1,2-tetrafluoroethane solvate

Micronised anhydrous beclomethasone dipropionate (24.1 mg) and lecithin (3.3 mg) were weighed into a clean dry plastic-coated glass bottle and dry (<50 ppm H$_2$O) 1,1,1,2-tetrafluoroethane (to 18.2 g) was added from a vacuum flask. The bottle was quickly sealed with a blank aluminium ferrule. The bottle was allowed to stand at ambient temperature. After several days, the solvate crystals were isolated by filtration. The crystal shape, infra-red spectrum and thermal analysis of the solvate obtained was substantially identical with the solvate of Example 1.

EXAMPLE 3

Aerosol Formulation

Micronised beclomethasone dipropionate-1,1,1,2-tetrafluoroethane solvate, prepared according to EXAMPLE 1 (31 mg), was weighed into a clean, dry, plastic-coated glass bottle and dry (<50 ppm H$_2$O) 1,1,1,2-tetrafluoroethane (18.2 g) was added from a vacuum flask. The bottle was quickly sealed with a blank aluminium ferrule. The resulting aerosol contained 0.138% (w/w) beclomethasone dipropionate (0.170% w/w solvate).

EXAMPLE 4

Aerosol Formulation

Micronised anhydrous beclomethasone dipropionate (60 mg), was weighed into a clean, dry, plastic-coated glass bottle and dry (<50 ppm H$_2$O) 1,1,1,2,3,3,3-heptafluoro-n-propane (18.2 g) was added from a vacuum flask. The bottle was quickly sealed with a blank aluminium ferrule. The resulting aerosol contained 0.33% (w/w) beclomethasone dipropionate.

We claim:

1. A pharmaceutical aerosol formulation which comprises particulate anhydrous beclomethasone dipropionate together with 1,1,1,2,3,3,3-heptafluoro-n-propane as propellant, which formulation is free of surfactant.

2. A formulation as claimed in claim 1 which contains 0.005–5.0% w/w of beclomethasone dipropionate relative to the total weight of the formulation.

3. A formulation as claimed in claim 1 wherein the particle size of the anhydrous beclomethasone dipropionate is such as to permit inhalation of substantially all of the drug into the lungs upon administration of the aerosol formulation.

4. A formulation as claimed in claim 2 wherein the particle size of the anhydrous beclomethasone dipropionate is such as to permit inhalation of substantially all of the drug into the lungs upon administration of the aerosol formulation.

5. A formulation as claimed in claim 1 which additionally contains salbutamol.

6. A formulation as claimed in claim 2 which additionally contains salbutamol.

7. A formulation as claimed in claim 3 which additionally contains salbutamol.

8. A pharmaceutical aerosol formulation which consists essentially of particulate anhydrous beclomethasone dipropionate and 1,1,1,2,3,3,3-heptafluoro-n-propane as propellant, which formulation is free of surfactant.

9. A canister suitable for delivering a pharmaceutical aerosol formulation which comprises a container capable of withstanding the vapor pressure of the propellant used, which container is closed with a metering valve and contains a pharmaceutical aerosol formulation as claimed in claim 1.

10. A canister suitable for delivering a pharmaceutical aerosol formulation which comprises a container capable of withstanding the vapor pressure of the propellant used, which container is closed with a metering valve and contains a pharmaceutical aerosol formulation as claimed in claim 8.

11. A metered dose inhaler which comprises a canister as claimed in claim 9 fitted into a suitable channeling device.

12. A method of treating respiratory disorders which comprises administration by inhalation of an effective amount of a pharmaceutical aerosol formulation as claimed in claim 1.

13. A method of treating respiratory disorders which comprises administration by inhalation of an effective amount of a pharmaceutical aerosol formulation as claimed in claim 8.

* * * * *